(12) United States Patent
Van Horn (10) Patent No.: US 11,213,105 B2
(45) Date of Patent: Jan. 4, 2022

(54) FEMININE HYGIENE STORAGE ASSEMBLY (71) Applicant: Eleanor Van Horn, Helena, AL (US)

(72) Inventor: Eleanor Van Horn, Helena, AL (US)

( * ) Notice: Subject to any disclaimer, the term of this patent is extended or adjusted under 35 U.S.C. 154(b) by 0 days.

(21) Appl. No.: 16/892,775

(22) Filed: Jun. 4, 2020

(65) Prior Publication Data

US 2021/0378374 A1 Dec. 9, 2021

(51) Int. Cl.
*A45C 11/00* (2006.01)
*A45C 13/02* (2006.01)
*A61F 15/00* (2006.01)

(52) U.S. Cl.
CPC ............ *A45C 11/008* (2013.01); *A45C 13/02* (2013.01); *A61F 15/001* (2013.01); *A45C 2011/007* (2013.01)

(58) Field of Classification Search
CPC ....... A45C 11/00; A45C 11/008; A45C 13/02; A45C 2011/007; A61F 15/00; A61F 15/001; B65D 69/00
USPC .......................................................... 206/581
See application file for complete search history.

(56) References Cited

U.S. PATENT DOCUMENTS

| | | | |
|---|---|---|---|
| 5,579,916 A | 12/1996 | Manko | |
| 6,164,451 A * | 12/2000 | Sherman | A45C 13/02 206/472 |
| 6,298,993 B1 * | 10/2001 | Kalozdi | A45C 3/00 150/106 |
| 7,104,977 B2 | 9/2006 | Price | |
| 7,144,391 B1 | 12/2006 | Kreutz | |
| D758,735 S | 6/2016 | Hernandez | |
| 2003/0136704 A1 | 7/2003 | Burgess | |
| 2004/0195135 A1 * | 10/2004 | Seamon | A45C 13/02 206/459.1 |
| 2007/0090014 A1 | 4/2007 | Wheeler | |
| 2011/0215025 A1 | 9/2011 | Gonzales | |
| 2013/0062246 A1 | 3/2013 | Staples | |
| 2015/0090629 A1 | 4/2015 | Diaz-Santiago | |

FOREIGN PATENT DOCUMENTS

WO WO0217844 3/2002

* cited by examiner

*Primary Examiner* — Bryon P Gehman (57) ABSTRACT

A feminine hygiene storage assembly for discretely transporting feminine hygiene products includes a case that has a first portion which is hingedly coupled to a second portion. A plurality of first pockets is each of the first pockets is coupled to the first portion of the case for containing feminine hygiene products. A plurality of second pockets and a third pocket is each coupled to the second portion of the case for containing feminine hygiene products. The third pocket is comprised of a fluid impermeable material to inhibit fluids in the soiled undergarments or used feminine hygiene products from escaping the third pocket. A suspension is coupled to the case and the suspension is extendable over a support to position the case at a convenient height for the user.

10 Claims, 6 Drawing Sheets

FEMININE HYGIENE STORAGE ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to hygiene storage devices and more particularly pertains to a new hygiene storage device for discretely storing and transporting feminine hygiene products.

(2) Description of Related Art Including Information Disclosed Under 37 CFR 1.97 and 1.98

The prior art relates to hygiene storage devices including a case with a zipper and pouches for storing feminine hygiene product and that has a loop for hanging the case on a support. The prior art also discloses a variety of pouches with closures for storing feminine hygiene products. The prior art does not disclose a hygiene storage case that has a fluid impermeable pouch and that is retained at a perpendicular angle when the case is opened to define a work surface.

BRIEF SUMMARY OF THE INVENTION

An embodiment of the disclosure meets the needs presented above by generally comprising a case that has a first portion which is hingedly coupled to a second portion. A plurality of first pockets is each of the first pockets is coupled to the first portion of the case for containing feminine hygiene products. A plurality of second pockets and a third pocket is each coupled to the second portion of the case for containing feminine hygiene products. The third pocket is comprised of a fluid impermeable material to inhibit fluids in the soiled undergarments or used feminine hygiene products from escaping the third pocket. A suspension is coupled to the case and the suspension is extendable over a support to position the case at a convenient height for the user.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
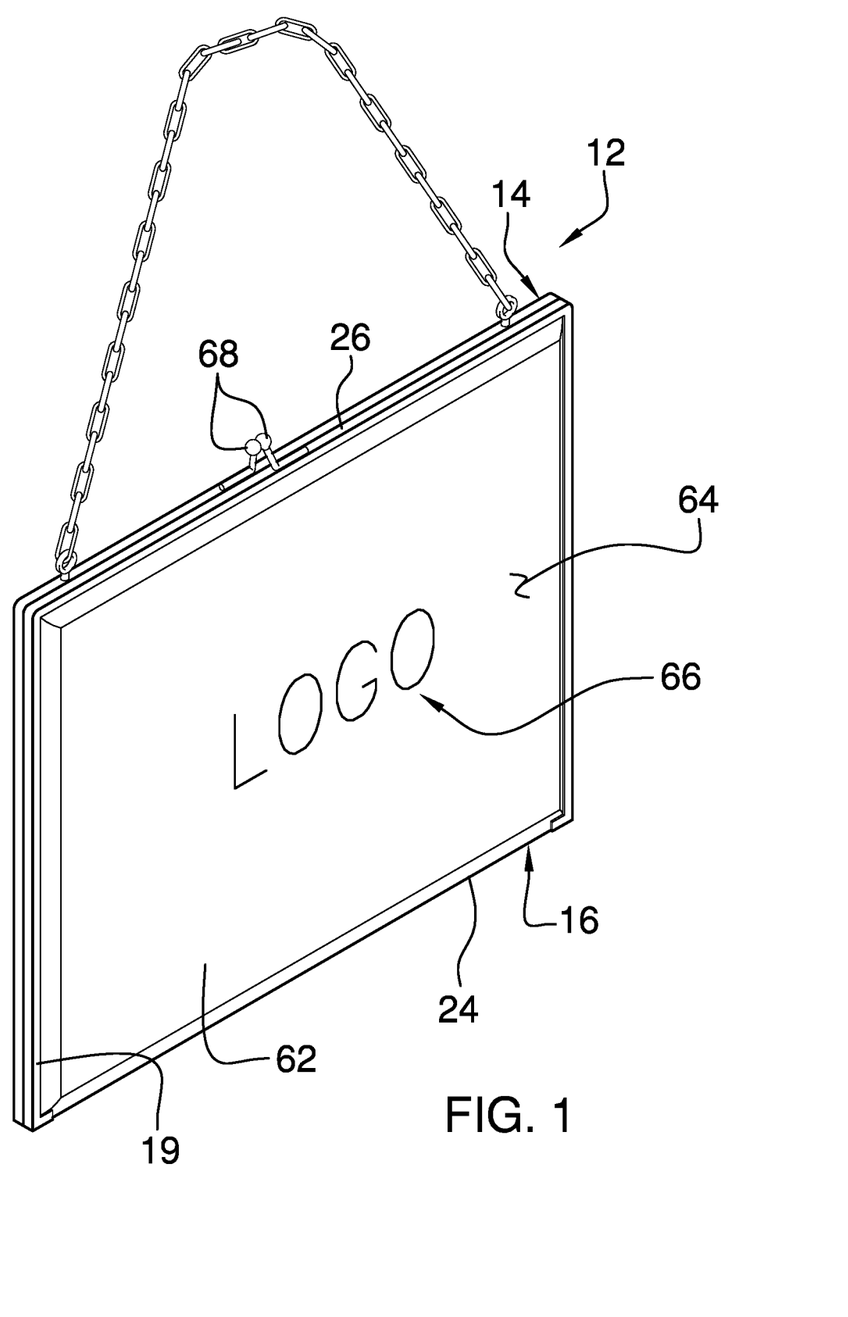
FIG. 1 is a front perspective view of a feminine hygiene storage assembly according to an embodiment of the disclosure showing a case in a closed position.
Figure 2:
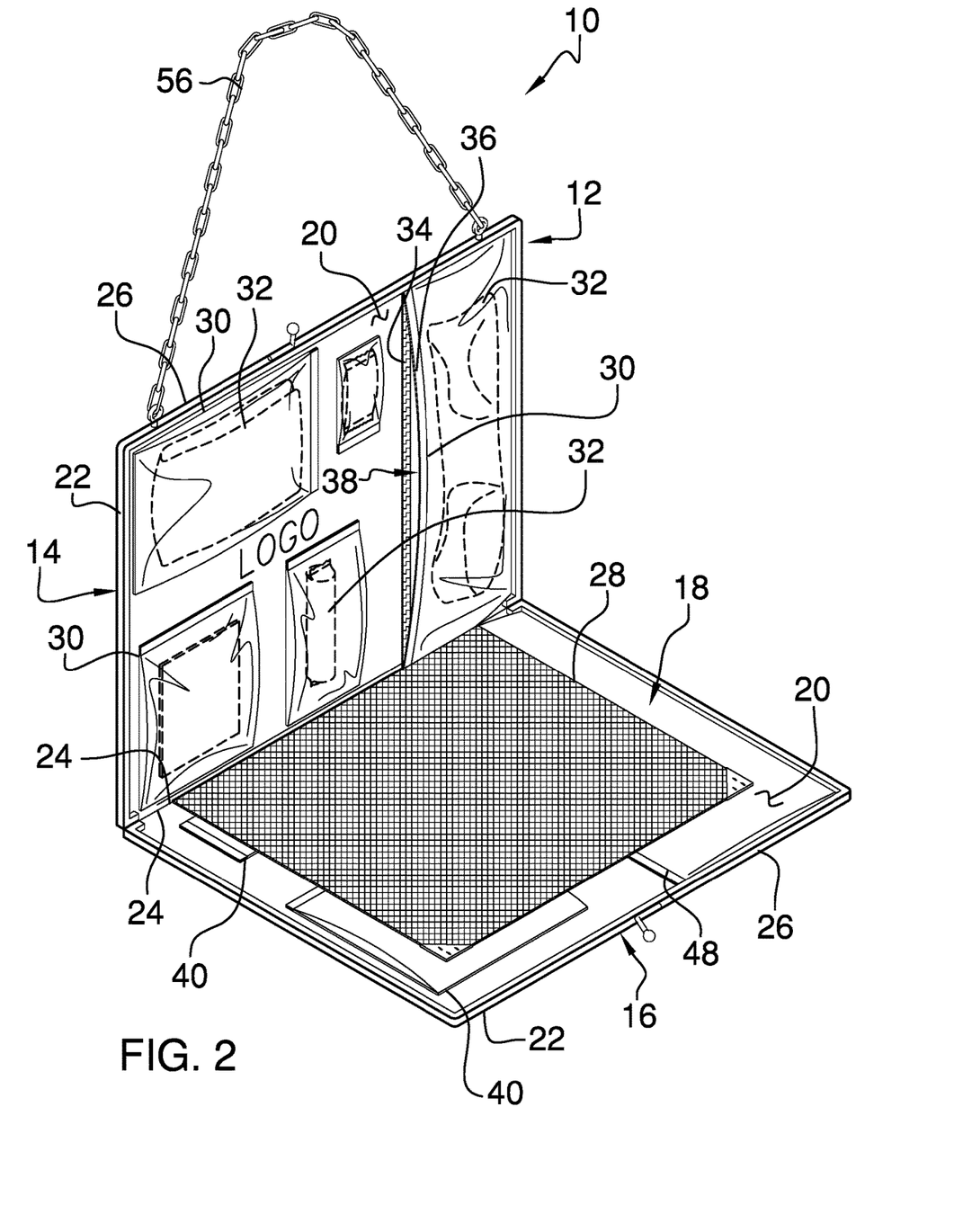
FIG. 2 is a front perspective view of an embodiment of the disclosure showing a case in an open position.
Figure 3:
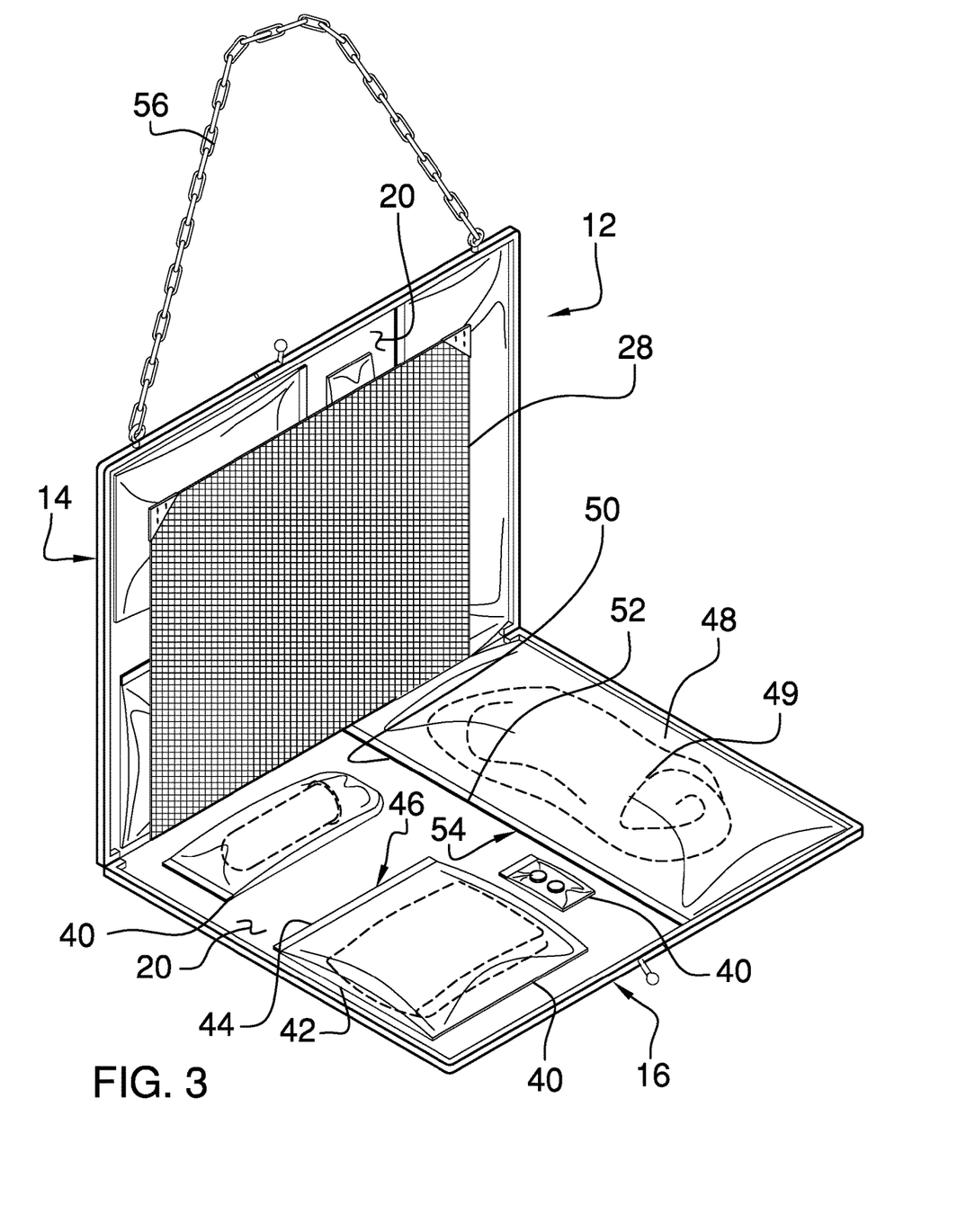
FIG. 3 is a front perspective view of an embodiment of the disclosure showing a mesh divider lifted against a first portion of a case.
Figure 4:
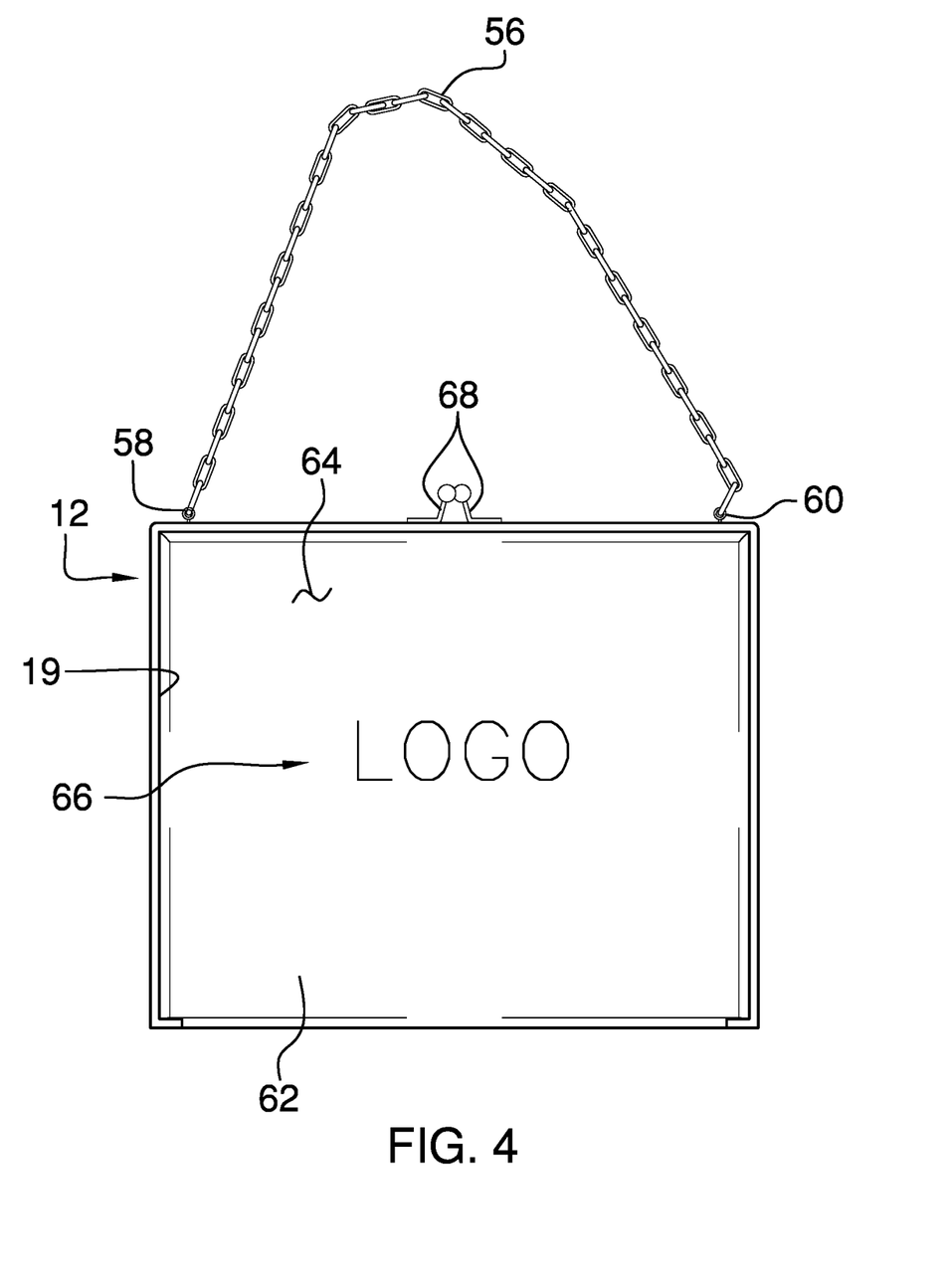
FIG. 4 is a front view of an embodiment of the disclosure.
Figure 5:
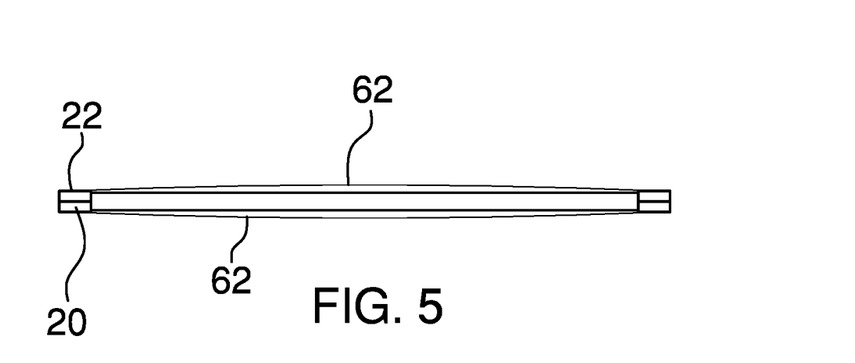
FIG. 5 is a bottom view of an embodiment of the disclosure.
Figure 6:
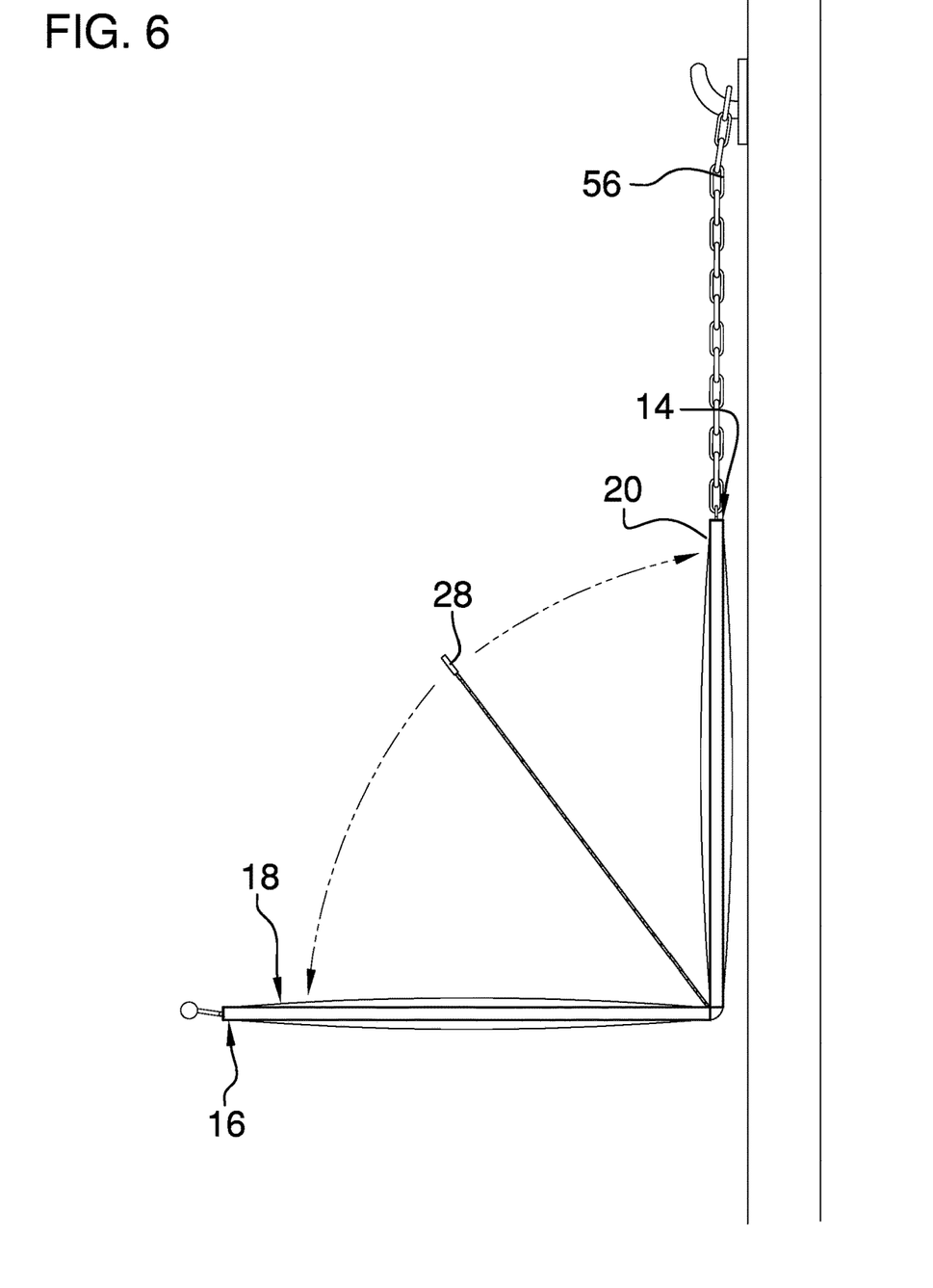
FIG. 6 is a perspective in-use view of an embodiment of the disclosure.

With reference now to the drawings, and in particular to FIGS. 1 through 6 thereof, a new hygiene storage device embodying the principles and concepts of an embodiment of the disclosure and generally designated by the reference numeral 10 will be described.

As best illustrated in FIGS. 1 through 6, the feminine hygiene storage assembly 10 generally comprises a case 12 that has a first portion 14 which is hingedly coupled to a second portion 16. The case 12 is positionable in an open position having the first portion 14 being retained at a right angle with the second portion 16. In this way the second portion 16 can define a horizontal work surface 18. The case 12 is positionable in a closed position having the first portion 14 resting against the second portion 16. Each of the first portion 14 and the second portion 16 may have a border 19 that extends substantially around each of the first portion 14 and the second portion 16.

Each of the first portion 14 and the second portion 16 has an upper surface 20, a lower surface 22, a rear edge 24 and a top edge 26. The rear edge 24 of the first portion 14 is hingedly coupled to the rear edge 24 of the second portion 16, and the upper surface 20 of the first portion 14 faces the upper surface 20 of the second portion 16 when the case 12 is in the closed position. The first portion 14 lies on a plane that is oriented perpendicular to the second portion 16 when the case 12 is in the open position. In this way the upper surface 20 of the second portion 16 defines the horizontal work surface 18 when the case 12 is in the open position. A mesh divider 28 is movably coupled to the case 12 and the mesh divider 28 is positioned between the first portion 14 and the second portion 16. Additionally, the mesh divider 28 is positionable to lie against the upper surface 20 of either of the first portion 14 or the second portion 16.

A plurality of first pockets 30 is each coupled to the first portion 14 of the case 12 for containing feminine hygiene products 32. The feminine hygiene products 32 may include tampons, maxi pads, cleaning wipes, clean undergarments and any other item commonly employed for feminine hygiene. Additionally, each of the first pockets 30 may be structured in various shapes and sizes for accommodating specific feminine hygiene products 32. Each of the first pockets 30 has a perimeter edge 34 that is coupled to the upper surface 20 of the first portion 14 and the perimeter edge 34 of each of the first pockets 30 has a first side 36. The first side 36 of the perimeter edge 34 of each of the first pockets 30 is uncoupled from the upper surface 20 of the first portion 14 to define an opening 38 into each of the first pockets 30. Moreover, the first side 36 is matable to the upper surface 20 of the first portion 14 for closing the first pockets 30. A plurality of mating members may be provided, including but not being limited to hook and loop fasteners or adhesive strips, for retaining the first pockets 30 in a closed condition.

A plurality of second pockets 40 is provided and each of the second pockets 40 is coupled to the second portion 16 of the case 12 for containing feminine hygiene products 32. Each of the second pockets 40 has a perimeter edge 42 that is coupled to the upper surface 20 of the second portion 16 and the perimeter edge 42 of each of the second pockets 40 has a first side 44. Moreover, the first side 44 of the perimeter edge 42 of each of the second pockets 40 is uncoupled from the upper surface 20 of the second portion 16 to define an opening 46 into each of the second pockets 40. The first side 44 of the perimeter edge 42 of each of the second pockets 40 is matable to the upper surface 20 of the second portion 16 for closing the second pockets 40. A plurality of mating members may be provided, including but not being limited to hook and loop fasteners or adhesive strips, for retaining the second pockets 40 in a closed condition.

A third pocket 48 is coupled to the second portion 16 of the case 12 to contain soiled undergarments 49 and used feminine hygiene products 32. The third pocket 48 is comprised of a fluid impermeable material to inhibit fluids in the soiled undergarments 49 or used feminine hygiene products 32 from escaping the third pocket 48. Additionally, the third pocket 48 is comprised of an opaque material to conceal the soiled undergarments 49 and the used feminine hygiene products 32. The opaque material may be a metallic foil or other similar type of material.

The third pocket 48 has a perimeter edge 50 is coupled to the upper surface 20 of the second portion 16 and the perimeter edge 50 of the third pocket 48 has a first side 52. The first side 52 of the perimeter edge 50 of the third pocket 48 is uncoupled from the upper surface 20 of the second portion 16 to define an opening 54 into the third pocket 48. The first side 52 of the perimeter edge 50 of the third pocket 48 is matable to the upper surface 20 of the second portion 16 for closing the third pocket 48. Moreover, the first side 52 of the perimeter edge 50 of the third pocket 48 forms a fluid impermeable seal with the upper surface 20 of the second portion 16. A mating member may be provided, including but not being limited to a tab and groove zipper, which forms a fluid impermeable seal when closed.

A suspension 56 is provided and the suspension 56 is coupled to the case 12. The suspension 56 is extendable over a support thereby facilitating the case 12 to be suspended from the support at a convenient height for the user. The suspension 56 has a first end 58 and a second end 60, and each of the first end 58 and the second end 60 is coupled to the top edge 26 of the first portion 14 such that the suspension 56 forms a loop. The suspension 56 may be a chain, a cable or any other type of flexible line. A pair of cushions 62 is each coupled to the lower surface 22 of a respective one of the first portion 14 and the second portion 16 of the case 12 and each the cushions 62 has an exposed surface 64 with respect to the lower surface 22. Each cushion 62 substantially covers the lower surface 22 and each cushion 62 is comprised of a resiliently compressible material. Moreover, the exposed surface 64 of each cushion 62 has logo indicia 66 printed thereon.

A pair of closures 68 is provided and each of the closures 68 is coupled to and extends away from the top edge 26 of a respective one of the first portion 14 and the second portion 16. Each of the closures 68 engages each other when the case 12 is in the closed position for retaining the case 12 in the closed position. Each of the closures 68 is disengageable from each other for opening the case 12. Each of the closures 68 may include a stem and a ball coupled to the stem. The stem of each of the closures 68 may be biased toward each other such that the balls rub past each other when the case 12 is closed or opened. Additionally, the closures 68 may comprise any type of releasable fastener.

In use, the feminine hygiene products 32 are stored in the first pockets 30 and the second pockets 40 and the case 12 is carried along with the user when the user is not at home, such as at work or an entertainment event. The case 12 is taken into a bathroom stall or the like and the suspension 56 is suspended over a coat hook or other support in the bathroom stall. The case 12 is opened and the second portion 16 of the case 12 defines the horizontal work surface 18. In this way the feminine hygiene products 32 are easily accessible to the user in the bathroom stall. The user can place used feminine hygiene products 32 and soiled undergarments 49 in the third pocket 48 to ensure neither odors nor fluids escape the third pocket 48.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:
1. A feminine hygiene storage assembly for storing feminine hygiene products and for defining a work surface when positioned in an open position, said assembly comprising:
   a case having a first portion being hingedly coupled to a second portion, said case being positionable in an open position having said first portion being retained at a right angle with said second portion thereby facilitating said second portion to define a horizontal work surface, said case being positionable in a closed position having said first portion resting against said second portion;
   a mesh divider being movably coupled to said case, said mesh divider being positioned between said first portion and said second portion;
   a plurality of first pockets, each of said first pockets being coupled to said first portion of said case wherein each of said first pockets is configured to contain feminine hygiene products;
   a plurality of second pockets, each of said second pockets being coupled to said second portion of said case wherein each of said second pockets is configured to contain feminine hygiene products;
   a third pocket being coupled to said second portion of said case wherein said third pocket is configured to contain soiled undergarments and used feminine hygiene products, said third pocket being comprised of a fluid impermeable material wherein said third pocket is configured to inhibit fluids in the soiled undergarments or used feminine hygiene products from escaping said third pocket, said third pocket being comprised of an opaque material wherein said third pocket is configured to conceal the soiled undergarments and the used feminine hygiene products; and
   a suspension being coupled to said case, said suspension being extendable over a support thereby facilitating said case to be suspended from the support wherein said case is configured to be positioned at a convenient height for a user.

2. The assembly according to claim 1, wherein each of said first portion and said second portion has an upper surface, a lower surface, a rear edge and a top edge, said rear edge of said first portion being hingedly coupled to said rear edge of said second portion, said upper surface of said first portion facing said upper surface of said second portion when said case is in said closed position, said upper surface of said second portion defining said horizontal work surface when said case is in said open position.

3. The assembly according to claim 2, wherein each of said first pockets has a perimeter edge being coupled to said upper surface of said first portion, said perimeter edge of each of said first pockets having a first side, said first side of said perimeter edge of each of said first pockets being uncoupled from said upper surface of said first portion to define an opening into each of said first pockets.

4. The assembly according to claim 2, wherein each of said second pockets has a perimeter edge being coupled to said upper surface of said second portion, said perimeter edge of each of said second pockets having a first side, said first side of said perimeter edge of each of said second pockets being uncoupled from said upper surface of said second portion to define an opening into each of said second pockets.

5. The assembly according to claim 2, wherein said third pocket has a perimeter edge being coupled to said upper surface of said second portion, said perimeter edge of said third pocket having a first side, said first side of said perimeter edge of said third pocket being uncoupled from said upper surface of said second portion to define an opening into said third pocket.

6. The assembly according to claim 5, wherein said first side of said perimeter edge of said third pocket forms a fluid impermeable seal with said upper surface of said second portion.

7. The assembly according to claim 2, wherein said suspension has a first end and a second end, each of said first end and said second end being coupled to said top edge of said first portion such that said suspension forms a loop.

8. The assembly according to claim 2, further comprising a pair of cushions, each of said cushions being coupled to said lower surface of a respective one of said first portion and said second portion of said case, each of said cushions having an exposed surface with respect to said lower surface, each of said cushions substantially covering said lower surface, each of said cushions being comprised of a resiliently compressible material, said exposed surface of each of said cushions having logo indicia being printed thereon.

9. The assembly according to claim 2, further comprising a pair of closures, each of said closures being coupled to and extending away from said top edge of a respective one of said first portion and said second portion, each of said closures engaging each other when said case is in said closed position tier retaining said case in said closed position, each of said closures being disengagable from each other for opening said case.

10. A feminine hygiene storage assembly for storing feminine hygiene products and for defining a work surface when positioned in an open position, said assembly comprising:
    a case having a first portion being hingedly coupled to a second portion, said case being positionable in an open position having said first portion being retained at a right angle with said second portion thereby facilitating said second portion to define a horizontal work surface, said case being positionable in a closed position having said first portion resting against said second portion, each of said first portion and said second portion having an upper surface, a lower surface, a rear edge and a top edge, said rear edge of said first portion being hingedly coupled to said rear edge of said second portion, said upper surface of said first portion facing said upper surface of said second portion when said case is in said closed position, said upper surface of said second portion defining said horizontal work surface when said case is in said open position;
    a mesh divider being movably coupled to said case, said mesh divider being positioned between said first portion and said second portion, said mesh divider being positionable to lie against said upper surface of each of said first portion or said second portion;
    a plurality of first pockets, each of said first pockets being coupled to said first portion of said case wherein each of said first pockets is configured to contain feminine hygiene products, each of said first pockets having a perimeter edge being coupled to said upper surface of said first portion, said perimeter edge of each of said first pockets having a first side, said first side of said perimeter edge of each of said first pockets being uncoupled from said upper surface of said first portion to define an opening into each of said first pockets;
    a plurality of second pockets, each of said second pockets being coupled to said second portion of said case wherein each of said second pockets is configured to contain feminine hygiene products, each of said second pockets having a perimeter edge being coupled to said upper surface of said second portion, said perimeter edge of each of said second pockets having a first side, said first side of said perimeter edge of each of said second pockets being uncoupled from said upper surface of said second portion to define an opening into each of said second pockets;

a third pocket being coupled to said second portion of said case wherein said third pocket is configured to contain soiled undergarments and used feminine hygiene products, said third pocket being comprised of a fluid impermeable material wherein said third pocket is configured to inhibit fluids in the soiled undergarments or used feminine hygiene products from escaping said third pocket, said third pocket being comprised of an opaque material wherein said third pocket is configured to conceal the soiled undergarments and the used feminine hygiene products, said third pocket having a perimeter edge being coupled to said upper surface of said second portion, said perimeter edge of said third pocket having a first side, said first side of said perimeter edge of said third pocket being uncoupled from said upper surface of said second portion to define an opening into said third pocket, said first side of said perimeter edge of said third pocket forming a fluid impermeable seal with said upper surface of said second portion;

a suspension being coupled to said case, said suspension being extendable over a support thereby facilitating said case to be suspended from the support wherein said case is configured to be positioned at a convenient height for a user, said suspension having a first end and a second end, each of said first end and said second end being coupled to said top edge of said first portion such that said suspension forms a loop;

a pair of cushions, each of said cushions being coupled to said lower surface of a respective one of said first portion and said second portion of said case, each of said cushions having an exposed surface with respect to said lower surface, each of said cushions substantially covering said lower surface, each of said cushions being comprised of a resiliently compressible material, said exposed surface of each of said cushions having logo indicia being printed thereon; and a pair of closures, each of said closures being coupled to and extending away from said top edge of a respective one of said first portion and said second portion, each of said closures engaging each other when said case is in said closed position for retaining said case in said closed position, each of said closures being disengagable from each other for opening said case.

\* \* \* \* \*